(12) United States Patent
Tsujii et al.

(10) Patent No.: US 9,049,996 B2
(45) Date of Patent: Jun. 9, 2015

(54) STEREOSCOPIC X-RAY IMAGING APPARATUS

(71) Applicant: CANON KABUSHIKI KAISHA, Tokyo (JP)

(72) Inventors: Osamu Tsujii, Kawasaki (JP); Takashi Ogura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 94 days.

(21) Appl. No.: 13/903,873

(22) Filed: May 28, 2013

(65) Prior Publication Data

US 2013/0322594 A1 Dec. 5, 2013

(30) Foreign Application Priority Data

May 31, 2012 (JP) ................. 2012-124101

(51) Int. Cl.
- *A61B 6/02* (2006.01)
- *A61B 6/08* (2006.01)
- *A61B 6/00* (2006.01)

(52) U.S. Cl.
CPC . *A61B 6/022* (2013.01); *A61B 6/08* (2013.01); *A61B 6/4007* (2013.01)

(58) Field of Classification Search
CPC .......... A61B 6/022; A61B 6/08; A61B 6/587; H04N 13/0246; H04N 13/0253; H04N 13/0003; G06T 7/0018; G06T 7/002
USPC ........................................... 378/41, 206, 207
See application file for complete search history.

(56) References Cited

FOREIGN PATENT DOCUMENTS

| JP | 2010115270 A | 5/2010 |
|----|--------------|--------|
| JP | 2010233875 A | 10/2010 |
| JP | 2011072369 A | 4/2011 |

*Primary Examiner* — Jurie Yun
(74) *Attorney, Agent, or Firm* — Canon USA Inc. IP Division (57) ABSTRACT

A stereoscopic X-ray imaging apparatus includes: right and left X-ray tubes; a diaphragm unit in which right and left openings are formed through which X-rays radiated by the right and left X-ray tubes pass, respectively; an X-ray sensor on which the X-ray radiated by each of the right and left X-ray tubes is projected; a controller configured to control positions and sizes of the right and left openings; and right and left visible light sources configured to radiate a visible light to the X-ray sensor in the same area as each of the right and left X-ray tubes through each of the right and left openings. Spectra of the visible light emitted by the right and left visible light sources are different from each other.

16 Claims, 7 Drawing Sheets

STEREOSCOPIC X-RAY IMAGING APPARATUS

BACKGROUND OF THE INVENTION

1. Field of the Invention

The present invention relates to a stereoscopic X-ray imaging apparatus.

2. Description of the Related Art

A stereoscopic X-ray imaging apparatus has an advantage of being capable of recognizing an anteroposterior relationship of a plurality of blood vessels. The stereoscopic X-ray imaging apparatus is configured to avoid unnecessary radiation exposure for an object (subject). Japanese Patent Application Laid-Open No. 2011-72369 discloses a configuration in which a three-dimensional position of a biopsy region is calculated based on two X-ray images obtained by stereoscopic imaging. Based on the calculated three-dimensional position of the biopsy region and a stereoscopic angle of a radiation source, a new X-ray radiation field is calculated. Japanese Patent Application Laid-Open No. 2010-233875 discloses a configuration in which an X-ray radiation field is controlled by a collimator to stay within a predetermined range. Japanese Patent Application Laid-Open No. 2010-115270 discloses a configuration in which a plurality of slits, through which an X-ray passes, is two-dimensionally formed in a collimator, and a size and a position of the plurality of slits are controlled.

In the X-ray imaging apparatus according to the related art having a stationary X-ray source (X-ray focus) and a stationary X-ray sensor, a position of each of the right and left X-ray sources for stereoscopic imaging is clear. Therefore, it is not necessary to distinguish between the radiation fields of the right and left X-ray sources. However, in an X-ray imaging apparatus having an X-ray source movable relative to an X-ray sensor, a three-dimensional positional relationship between the X-ray source and the X-ray sensor may not always be clear. For this reason, especially in stereoscopic X-ray imaging, it is necessary to set an appropriate angle of convergence and avoid the unnecessary radiation exposure due to a difference between the right and left X-ray radiation fields. Thus, a unit for appropriately and conveniently adjusting the positional relationship between the right and left X-ray sources is necessary for performing the effective stereoscopic X-ray imaging.

SUMMARY OF THE INVENTION

An exemplary object of the present invention for solving the above problem is to provide a stereoscopic X-ray imaging apparatus capable of appropriately and conveniently adjusting a positional relationship between right and left X-ray sources in stereoscopic X-ray imaging.

To solve the above problem, the present invention includes: a plurality of X-ray sources; a diaphragm unit in which a plurality of openings is formed, X-rays radiated by the plurality of X-ray sources passing through the plurality of openings, respectively; an X-ray sensor on which the X-ray radiated by each of the plurality of X-ray sources is projected; a controller configured to control positions and sizes of the plurality of openings; and a plurality of visible light sources configured to radiate a visible light to the X-ray sensor in the same area as each of the plurality of X-ray sources through each of the plurality of openings. Spectra of the visible light emitted by the plurality of visible light sources are different from each other.

Further features of the present invention will become apparent from the following description of exemplary embodiments (with reference to the attached drawings).

DESCRIPTION OF THE EMBODIMENTS

First Embodiment

Figure 1:
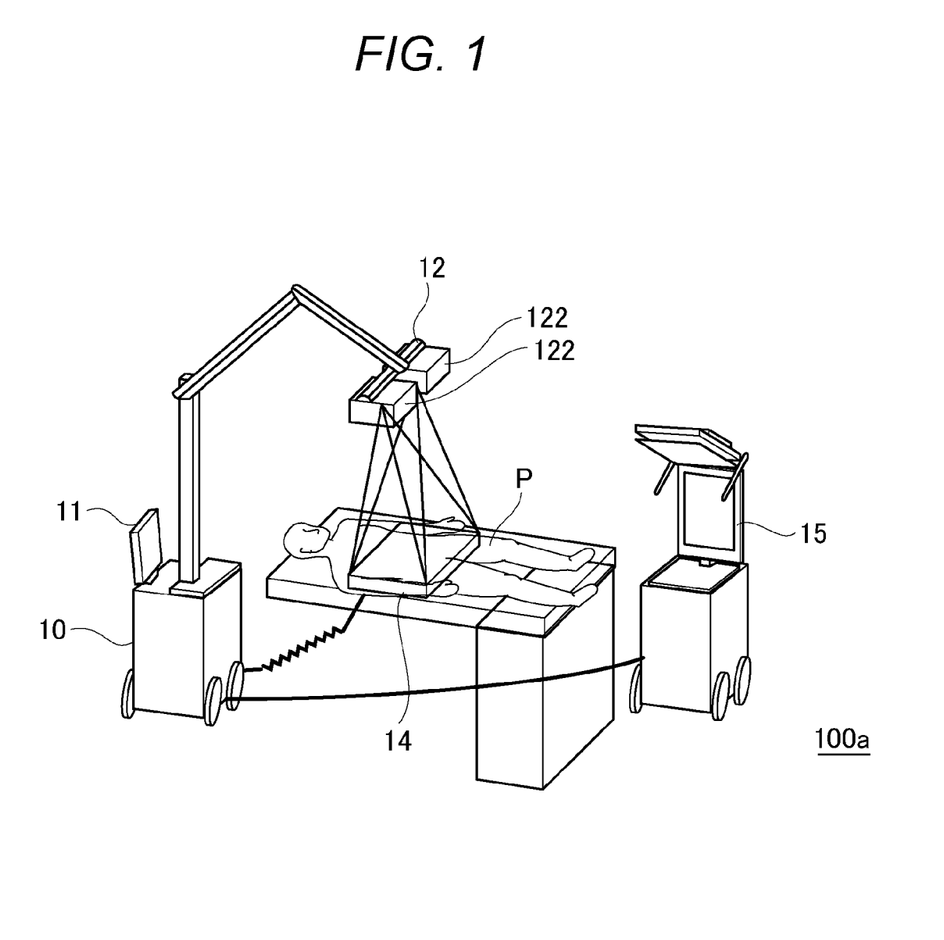
FIG. 1 is a schematic external view of a configuration of a stereoscopic X-ray imaging apparatus according to a first embodiment of the present invention.
Figure 2:
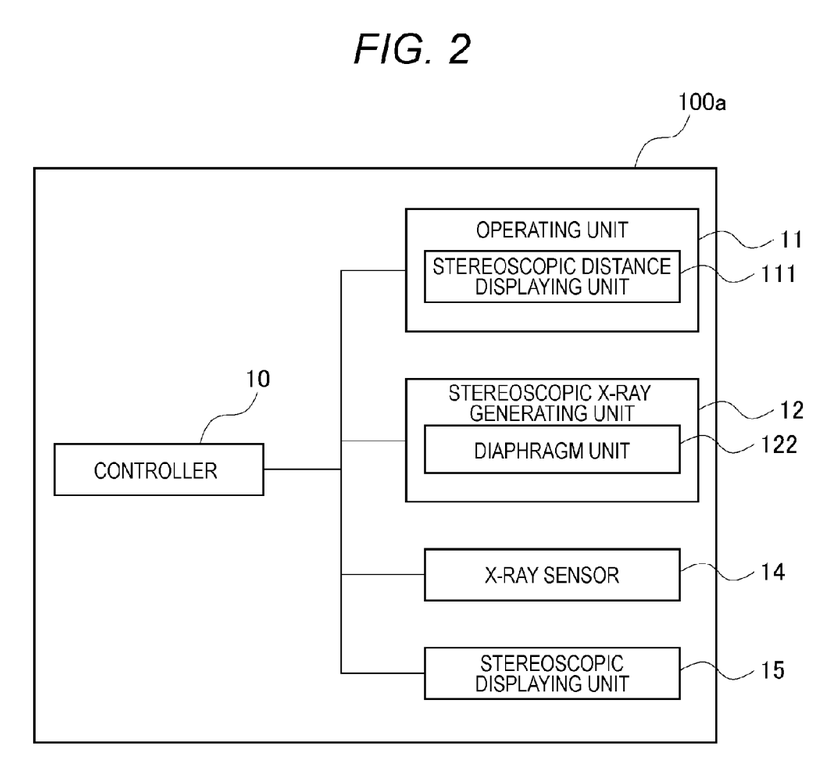
FIG. 2 is a block diagram of the stereoscopic X-ray imaging apparatus according to the first embodiment of the present invention.

First, a configuration of a stereoscopic X-ray imaging apparatus 100a according to a first embodiment of the present invention is described herein with reference to FIGS. 1 and 2. FIG. 1 is a schematic external view of the configuration of the stereoscopic X-ray imaging apparatus 100a according to the first embodiment of the present invention. FIG. 2 is a block diagram of the stereoscopic X-ray imaging apparatus 100a according to the first embodiment of the present invention. As in FIGS. 1 and 2, the stereoscopic X-ray imaging apparatus 100a includes an operating unit 11, a controller 10, a stereoscopic X-ray generating unit 12, an X-ray sensor 14, and a stereoscopic displaying unit 15.

The operating unit 11 is a unit to be used by an operator for operating the stereoscopic X-ray imaging apparatus 100a. The operating unit 11 includes an operating member (e.g., operation panel) to be operated by the operator, and a displaying unit (e.g., display panel) for displaying an operation menu. The operating unit 11 further includes a function of a stereoscopic distance displaying unit 111 for displaying an "appropriate stereoscopic diaphragm distance $D_j$". Details of the "appropriate stereoscopic diaphragm distance $D_j$" will be described later.

The controller 10, in response to an operation of the operating unit 11 by the operator, controls the stereoscopic X-ray imaging apparatus 100a (the stereoscopic X-ray generating unit 12, the X-ray sensor 14, and the stereoscopic displaying unit 15). The controller 10 is a computer having a CPU for performing predetermined arithmetic processing, and a storage device for storing a program and various data. The CPU of the controller 10 executes control of the stereoscopic X-ray imaging apparatus 100a by reading and executing the program from the storage device.

The stereoscopic X-ray generating unit 12 generates a stereoscopic X-ray, and radiates the generated stereoscopic X-ray to an object P and a surface of the X-ray sensor 14. Details of the stereoscopic X-ray generating unit 12 will be described later.

The X-ray sensor 14 receives the X-ray (X-ray that has passed through the object P) radiated by the stereoscopic X-ray generating unit 12, and converts the received X-ray into an image signal (electric signal). The image signal converted by the X-ray sensor 14 is sent to the controller 10, and predetermined image processing is performed thereon in the controller 10. The image signal, on which the predetermined image processing has been performed, is further sent to the stereoscopic displaying unit 15.

The stereoscopic displaying unit 15 stereoscopically displays the image signal sent from the controller 10. The stereoscopic displaying unit 15 includes the display panel, which can display an image.

Figure 3:
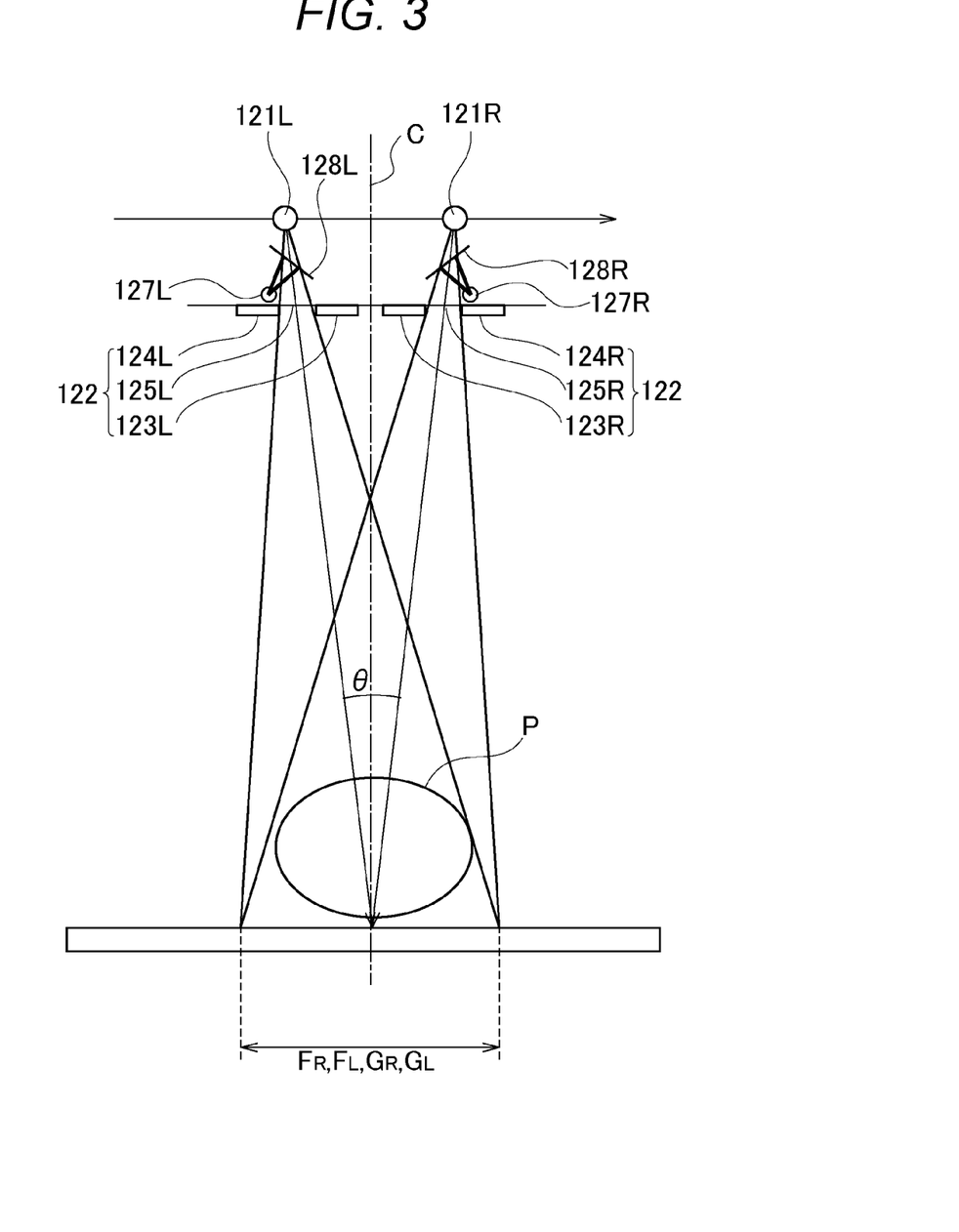
FIG. 3 is a schematic cross-sectional view of a configuration of a stereoscopic X-ray generating unit.

Next, a configuration of the stereoscopic X-ray generating unit 12 is described with reference to FIG. 3. FIG. 3 is a schematic cross-sectional view illustrating the configuration of the stereoscopic X-ray generating unit 12. As in FIG. 3, the stereoscopic X-ray generating unit 12 includes: (a plurality of) right and left X-ray tubes 121R and 121L, (a plurality of) right and left visible light sources 127R and 127L, (a plurality of) right and left X-ray transmissive mirrors 128R and 128L, and a diaphragm unit 122 (collimator). Each of the (plurality of) right and left X-ray tubes 121R and 121L is an X-ray source (X-ray focus), which alternately radiates the X-ray. Each of the (plurality of) right and left visible light sources 127R and 127L emits a visible light. The (plurality of) right and left X-ray transmissive mirrors 128R and 128L are disposed on paths of the X-rays radiated by the right and left X-ray tubes 121R and 121L, respectively. Then, the right and left X-ray transmissive mirrors 128R and 128L transmit the X-rays radiated by the right and left X-ray tubes 121R and 121L, and reflect the visible light emitted by the right and left visible light sources 127R and 127L, respectively. Note that the right and left visible light sources 127R and 127L are disposed at conjugate positions relative to the right and left X-ray tubes 121R and 121L, respectively.

The diaphragm unit 122 (collimator) defines a range of the X-ray radiated by each of the right and left X-ray tubes 121R and 121L. In the diaphragm unit 122, right and left inner blades 123R and 123L and right and left outer blades 124R and 124L are movably provided for blocking the X-ray. A right opening 125R is formed between the right inner blade 123R and the right outer blade 124R. A left opening 125L is formed between the left inner blade 123L and the left outer blade 124L. The X-ray and the visible light can pass through the right and left openings 125R and 125L. Positions and sizes of right and left X-ray radiation fields $G_R$ and $G_L$ (areas irradiated with X-ray radiation) and positions and sizes of right and left visible light projection fields $F_R$ and $F_L$ (areas irradiated with visible light radiation) are determined by positions and sizes of the right and left openings 125R and 125L. The operator can change the positions and the sizes of the right and left openings 125R and 125L by moving and positioning the right and left inner blades 123R and 123L and the right and left outer blades 124R and 124L. Accordingly, the operator can adjust positions and ranges of the right and left X-ray radiation fields $G_R$ and $G_L$, and positions and ranges of the visible light projection fields $F_R$ and $F_L$.

Note that the diaphragm unit 122 is provided with a driving mechanism for driving the right and left inner blades 123R and 123L and the right and left outer blades 124R and 124L. This driving mechanism is controlled by the controller 10. Therefore, the operator can adjust the positions and the ranges of the right and left X-ray radiation fields $G_R$ and $G_L$ by operating the operating unit 11. In addition, it is also possible to configure the right and left inner blades 123R and 123L and the right and left outer blades 124R and 124L to be manually operated by the operator in the moving and positioning thereof.

The X-rays radiated by the right and left X-ray tubes 121R and 121L transmit the right and left X-ray transmissive mirrors 128R and 128L, respectively. The X-ray is shaped by the diaphragm unit 122, and reaches the surface of the X-ray sensor 14. The visible light emitted by the right and left visible light sources 127R and 127L is reflected by the right and left X-ray transmissive mirrors 128R and 128L, respectively. The visible light is shaped by the diaphragm unit 122, and reaches the X-ray sensor 14. As described above, the right and left X-ray tubes 121R and 121L, and the right and left visible light sources 127R and 127L are disposed at the conjugate positions. Therefore, the X-ray radiation fields $G_R$ and $G_L$ correspond with the visible light projection fields $F_R$ and $F_L$. Thus, by visually recognizing the positions and the ranges of the right and left visible light projection fields $F_R$ and $F_L$, the operator can check the positions and the ranges of the right and left X-ray radiation fields $G_R$ and $G_L$. Then, the operator adjusts positions of the right and left inner blades 123R and 123L and the right and left outer blades 124R and 124L so that the right and left visible light projection fields $F_R$ and $F_L$ overlap (correspond) with each other on the surface of the X-ray sensor 14.

A spectrum of the visible light emitted by each of the right and left visible light sources 127R and 127L is different from each other. According to such a configuration, the operator can easily distinguish between the visible light projection fields $F_R$ and $F_L$ of the right and left visible light sources 127R and 127L. Thus, it becomes easier to adjust the positions and the sizes of the right and left X-ray radiation fields $G_R$ and $G_L$. In addition, a configuration is also possible in which a filter is disposed on a path of the visible light in or near the diaphragm unit 122. Each filter transmits the visible light having a spectrum different from each other. Such a configuration also enables the operator to easily distinguish between the visible light projection fields $F_R$ and $F_L$ of the right and left visible light sources 127R and 127L.

Note that in the case of using an anti-scatter grid having a specified grid distance, the operator moves the right and left inner blades 123R and 123L and the right and left outer blades 124R and 124L so that the "appropriate stereoscopic diaphragm distance $D_j$" equals the grid distance. At this time, the operator moves the right and left inner blades 123R and 123L and the right and left outer blades 124R and 124L while checking the "appropriate stereoscopic diaphragm distance $D_j$" displayed on the stereoscopic distance displaying unit 111. In this way, the positions and the sizes of the right and left visible light projection fields $F_R$ and $F_L$ can be adjusted to overlap (correspond) with each other on the surface of the X-ray sensor 14.

As in FIG. 3, the right and left openings 125R and 125L are symmetrically configured about a center line C, which runs in the middle of the right and left X-ray tubes 121R and 121L (right and left X-ray foci). In other words, the openings 125R and 125L of the same size are formed at positions symmetrical about the center line C. In order to realize such a configuration, the inner blades 123R and 123L are disposed at the positions symmetrical about the center line C, and move the same distance in opposite directions simultaneously or in a linked manner. Likewise, the right and left outer blades 124R and 124L are also disposed at the positions symmetrical about the center line C, and move the same distance in opposite directions simultaneously or in a linked manner. Note, however, that the moving distance of the inner blades 123R and 123L is different from the moving distance of the outer blades 124R and 124L. In a configuration in which the controller 10 controls the diaphragm unit 122, the controller 10 drives the right and left inner blades 123R and 123L to move them over the same distance in the opposite directions from each other, and also drives the right and left outer blades 124R and 124L to move them over the same distance in the opposite directions from each other. Furthermore, in a configuration in which the operator manually adjusts the diaphragm unit 122, a configuration may be applied in which the right and left inner blades 123R and 123L are linked by a linkage mechanism, and the right and left outer blades 124R and 124L are also linked by the linkage mechanism. Then, when the operator manually moves either one of the right and left inner blades 123R and 123L, the other of the right and left inner blades 123R and 123L moves the same distance in the opposite direction by the linkage mechanism. Likewise, when the operator manually moves either one of the right and left outer blades 124R and 124L, the other of the right and left outer blades 124R and 124L moves the same distance in the opposite direction by the linkage mechanism. With such a configuration, the right and left openings 125R and 125L have the same size, and are formed at positions symmetrical about the center line C.

Figure 4A:
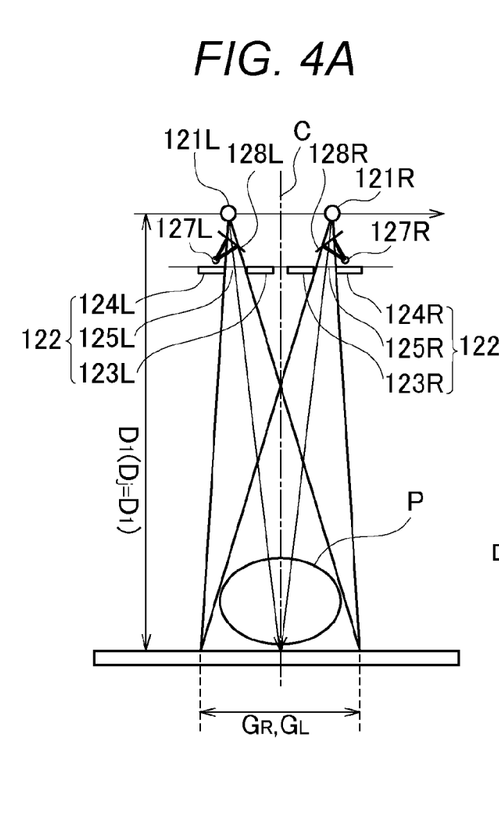
FIGS. 4A to 4C are schematic cross-sectional views illustrating a relationship between a distance (imaging distance) from right and left X-ray tubes to a surface of an X-ray sensor, and a position and a size of a visible light projection field (X-ray radiation field)
Figure 4B:
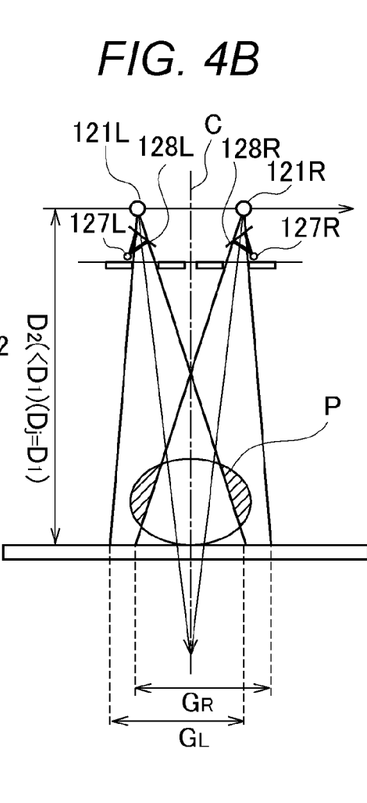
Figure 4C:
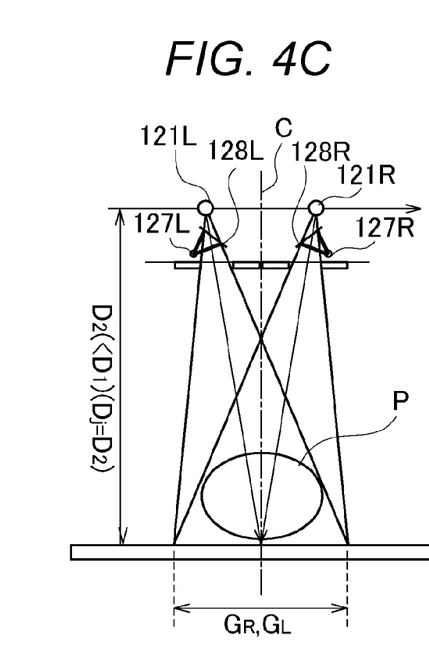

Next, control of the right and left openings 125R and 125L is described with reference to FIGS. 4A to 4C. FIGS. 4A to 4C are schematic cross-sectional views illustrating a relationship between a distance (imaging distance) from the right and left X-ray tubes 121R and 121L to the surface of the X-ray sensor 14, and the positions and the sizes of the visible light projection fields $F_R$ and $F_L$ (X-ray radiation fields $G_R$ and $G_L$).

The operator adjusts the positions and the sizes of the right and left X-ray radiation fields $G_R$ and $G_L$ by changing the positions and the sizes of the right and left openings 125R and 125L. Note that the right and left X-ray tubes 121R and 121L are not used for adjusting the positions and the sizes of the right and left X-ray radiation fields $G_R$ and $G_L$, but the right and left visible light sources 127R and 127L are used. As described above, the positions and the sizes of the right and left visible light projection fields $F_R$ and $F_L$ and the positions and the sizes of the right and left X-ray radiation fields $G_R$ and $G_L$ are the same. Therefore, the positions and the sizes of the right and left X-ray radiation fields $G_R$ and $G_L$ are adjusted by adjusting the positions and the sizes of the right and left visible light projection fields $F_R$ and $F_L$.

FIG. 4A is a schematic view illustrating a condition in which the imaging distance (SDD: Source Detector Distance) is $D_1$ and the "appropriate stereoscopic diaphragm distance $D_j$" is adjusted to $D_1$. Here, the "appropriate stereoscopic diaphragm distance $D_j$" refers to an imaging distance in which the right and left X-ray radiation fields $G_R$ and $G_L$ overlap (correspond) with each other on the surface of the X-ray sensor 14. The "appropriate stereoscopic diaphragm distance $D_j$" changes with the positions and the sizes of the openings 125R and 125L in the diaphragm unit 122. Thus, the operator can change the "appropriate stereoscopic diaphragm distance $D_j$" by changing the positions and the sizes of the openings 125R and 125L in the diaphragm unit 122 (by moving the inner blades 123R and 123L and the outer blades 124R and 124L). The operator changes the "appropriate stereoscopic diaphragm distance $D_j$" to correspond with the actual imaging distance. Accordingly, the stereoscopic X-ray imaging can be performed in an appropriate condition.

In a condition illustrated in FIG. 4A, the right and left visible light projection fields $F_R$ and $F_L$ (right and left X-ray radiation fields $G_R$ and $G_L$) overlap with each other on the surface of the X-ray sensor 14. Furthermore, in this condition, the visible light radiated by the right and left visible light sources 127R and 127L irradiates the object P entirely. In such a condition, the stereoscopic distance displaying unit 111 displays $D_1$ as the "appropriate stereoscopic diaphragm distance $D_j$". Note that the relationship between the positions and the sizes of the right and left openings 125R and 125L (positions of the inner blades 123R and 123L and the outer blades 124R and 124L) and the "appropriate stereoscopic diaphragm distance $D_j$" is stored in the controller 10. Then, when the diaphragm unit 122 is operated by the operator, the controller 10 detects (or calculates, based on the amount of movement) the positions and the sizes of the openings 125R and 125L. Then, the controller 10 reads the "appropriate stereoscopic diaphragm distance $D_j$" corresponding to the detected (or calculated) positions and sizes, and displays the distance on the stereoscopic distance displaying unit 111.

FIG. 4B is a schematic view illustrating a condition in which the imaging distance is changed to a distance $D_2$ ($D_2 < D_1$), which is smaller than the "appropriate stereoscopic diaphragm distance $D_j$", when the "appropriate stereoscopic diaphragm distance $D_j$" is adjusted to $D_1$. As in FIG. 4B, when the imaging distance becomes smaller than the "appropriate stereoscopic diaphragm distance $D_j$", the right and left visible light projection fields $F_R$ and $F_L$ (right and left X-ray radiation fields $G_R$ and $G_L$) are shifted either to the right or left on the surface of the X-ray sensor 14. Furthermore, on the object P, there is an area on which only the visible light from either one of the right and left visible light sources 127R and 127L is radiated, and not the visible light from the other (hatched areas in FIG. 4B). It is not possible to stereoscopically view this area. In this way, unnecessary radiation exposure (exposure not contributing to a stereoscopic view) occurs on the object P.

Therefore, as in FIG. 4C, the controller 10 or the operator adjusts the "appropriate stereoscopic diaphragm distance $D_j$" to be equal to the actual imaging distance. FIG. 4C illustrates a condition in which the "appropriate stereoscopic diaphragm distance $D_j$" is adjusted to $D_2$ when the imaging distance is $D_2$. As in FIG. 4C, when the "appropriate stereoscopic diaphragm distance $D_j$" and the actual imaging distance are the same, the X-ray is radiated on the object P entirely from both of the right and left X-ray tubes 121R and 121L. Therefore, it is possible to stereoscopically view the entire object P. Furthermore, no unnecessary radiation exposure occurs on the object P.

Second Embodiment

Figure 5:
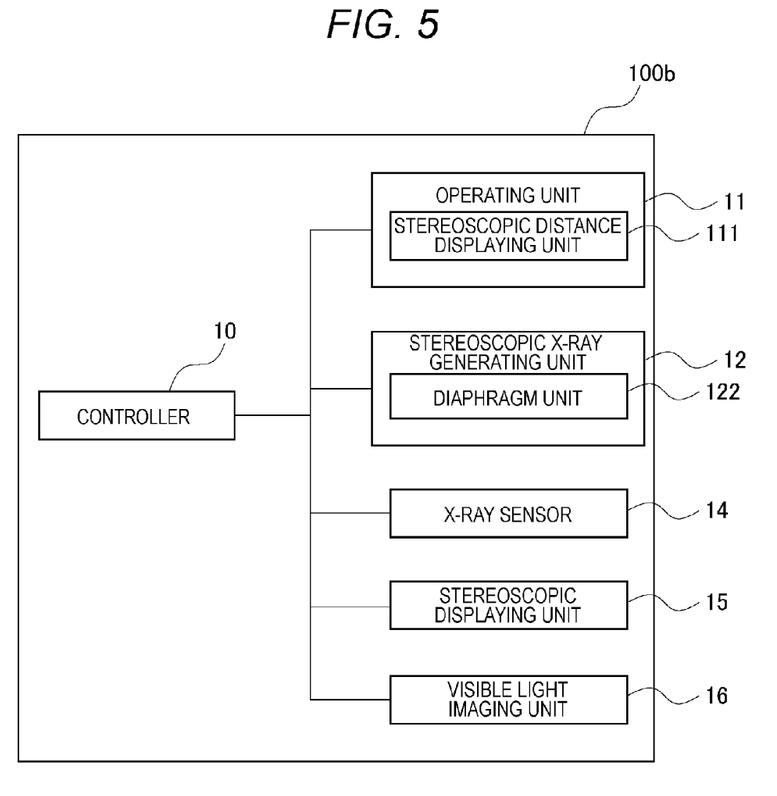
FIG. 5 is a schematic block diagram illustrating a configuration of a stereoscopic X-ray imaging apparatus according to a second embodiment.

Next, a second embodiment of the present invention is described. The first embodiment is a configuration in which an operator adjusts positions and ranges of the visible light projection fields $F_R$ and $F_L$ on the surface of the X-ray sensor 14. On the other hand, the second embodiment is a configuration in which a stereoscopic X-ray imaging apparatus 100b automatically performs an adjustment. FIG. 5 is a schematic block diagram of the configuration of the stereoscopic X-ray imaging apparatus 100b according to the second embodiment. Note that any part of the configuration common with the first embodiment is denoted with the same reference numeral and the description thereof is omitted (see FIG. 2).

As in FIG. 5, the stereoscopic X-ray imaging apparatus 100b includes a visible light imaging unit 16 (visible light image capturing unit). The visible light imaging unit 16 (visible light image capturing unit) is capable of imaging a visible light image (a composition image of the right and left visible light projection fields $F_R$ and $F_L$) projected onto a surface of the X-ray sensor 14. Various cameras with sensitivity to a visible light range are applicable as the visible light imaging unit 16 (visible light image capturing unit). Note that the visible light imaging unit is disposed, for example, in the stereoscopic X-ray generating unit 12 so as to image the visible light image projected onto the surface of the X-ray sensor 14. Note, however, that a specific position to dispose the visible light imaging unit 16 is not limited as long as it is capable of imaging the visible light image projected onto the surface of the X-ray sensor 14.

Figure 6A:
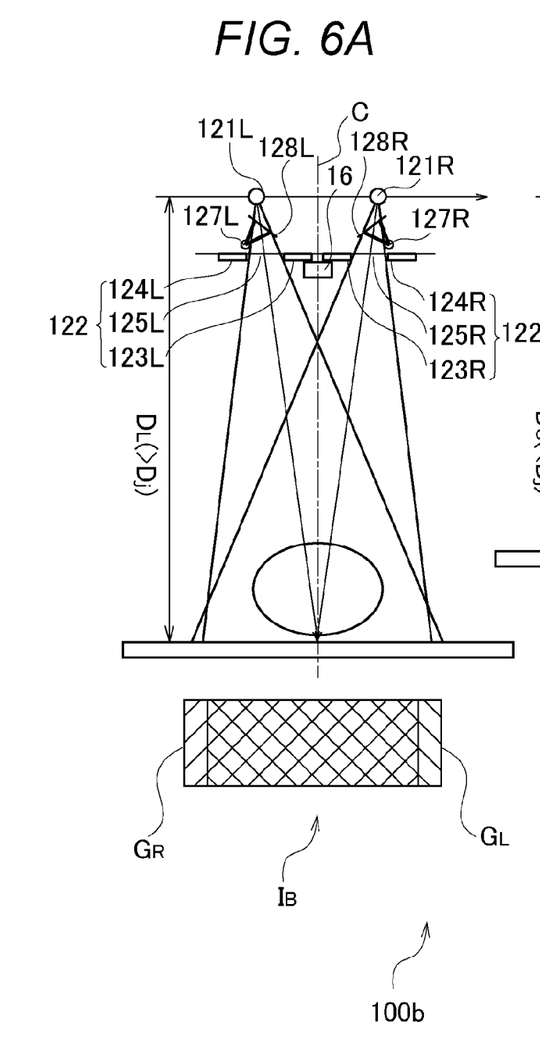
FIG. 6A is a schematic view illustrating a condition in which an "appropriate stereoscopic diaphragm distance" is smaller than an actual imaging distance, and an exemplary visible light image imaged by a visible light imaging unit in such a condition.
Figure 6B:
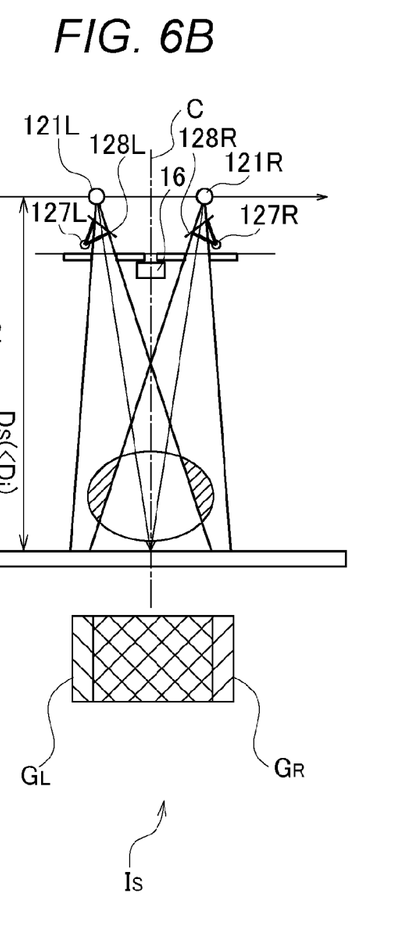
FIG. 6B is a schematic view illustrating a condition in which an "appropriate stereoscopic diaphragm distance" is larger than an actual imaging distance, and an exemplary visible light image imaged by the visible light imaging unit in such a condition.

FIG. 6A is a schematic view illustrating a condition in which the "appropriate stereoscopic diaphragm distance $D_j$" is smaller than an actual imaging distance $D_L$, and an exemplary visible light image $I_L$ imaged by the visible light imaging unit 16 in such a condition. FIG. 6B is a schematic view illustrating the condition in which the "appropriate stereoscopic diaphragm distance $D_j$" is larger than an actual imaging distance $D_s$, and an exemplary visible light image $I_s$ imaged by the visible light imaging unit 16 in such a condition.

A method of adjusting positions of the right and left X-ray radiation fields $G_R$ and $G_L$ in the stereoscopic X-ray imaging apparatus 100b according to the second embodiment is as follows.

First, by an operation of an operating unit by an operator, a controller 10 turns on the right and left visible light sources 127R and 127L. Accordingly, a visible light is radiated on the surface of the X-ray sensor 14, and a visible light image is formed thereon (right and left visible light projection fields $F_R$ and $F_L$ are combined). Then, the visible light imaging unit 16 images the visible light image formed on the surface of the X-ray sensor 14, and sends the imaged visible light image to the controller 10. The controller 10 determines a condition of overlapping between the right and left visible light projection fields $F_R$ and $F_L$ in the visible light image. Then, based on the determination result of the condition of overlapping, the controller 10 drives the diaphragm unit 122 to adjust the "appropriate stereoscopic diaphragm distance $D_j$".

Specifically, as in FIG. 6A, in a case where a side-to-side positional relationship of the right and left visible light sources 127R and 127L and the side-to-side positions of the right and left visible light projection fields $F_R$ and $F_L$ in the visible light image are reversed, the "appropriate stereoscopic diaphragm distance $D_j$" is smaller than the actual imaging distance. Therefore, in this case, the controller 10 drives the right and left inner blades 123R and 123L and the right and left outer blades 124R and 124L to increase the "appropriate stereoscopic diaphragm distance $D_j$". On the other hand, as in FIG. 6B, in a case where the positions of the right and left visible light sources 127R and 127L and the right and left positions of the right and left visible light projection fields $F_R$ and $F_L$ in the visible light image are not reversed, the "appropriate stereoscopic diaphragm distance $D_j$" is larger than the actual imaging distance. Therefore, in this case, the controller 10 drives the right and left inner blades 123R and 123L and the right and left outer blades 124R and 124L to decrease the "appropriate stereoscopic diaphragm distance $D_j$".

Then, the controller 10 repeatedly executes determination of the condition of overlapping between the visible light projection field $F_R$ and $F_L$ in the visible light image, and a change of the "appropriate stereoscopic diaphragm distance $D_j$". Accordingly, the controller 10 can converge the "appropriate stereoscopic diaphragm distance $D_j$" to the actual imaging distance.

Note that the controller 10 may also be configured to adjust the imaging distance to converge into the "appropriate stereoscopic diaphragm distance $D_j$" by driving and moving the stereoscopic X-ray generating unit 12 or the X-ray sensor 14.

Third Embodiment

Figure 7:
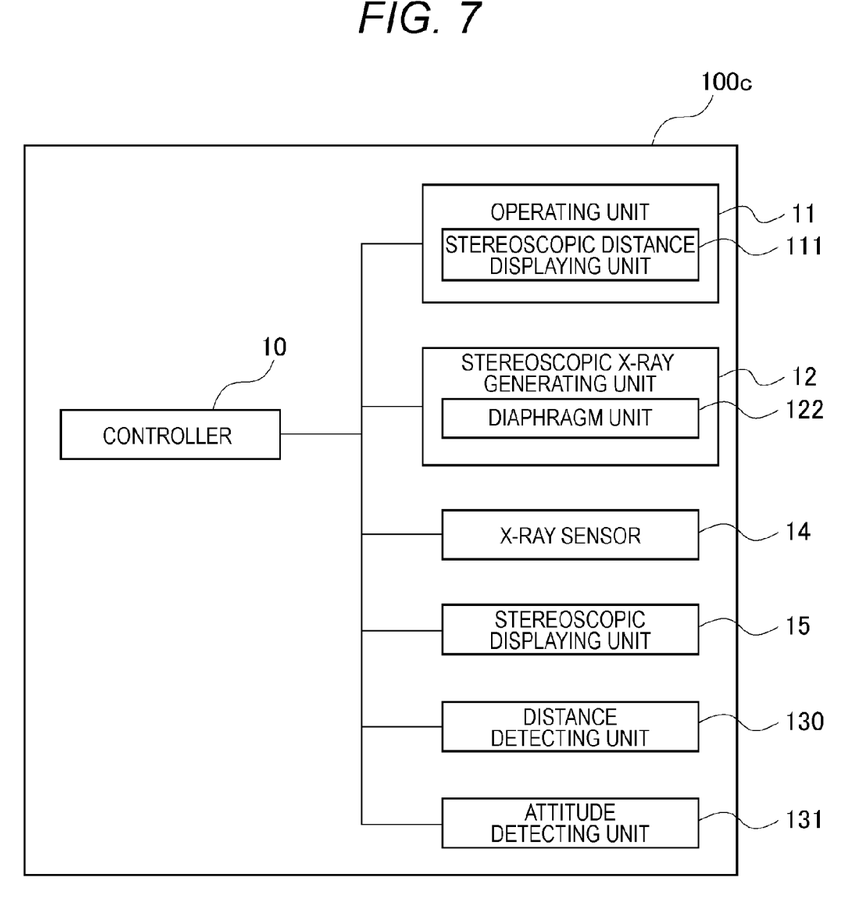
FIG. 7 is a block diagram of a stereoscopic X-ray imaging apparatus according to a third embodiment.

Next, a third embodiment of the present invention is described. The first and second embodiments assume a case where an imaging distance is not clear. On the other hand, in the third embodiment, a stereoscopic X-ray imaging apparatus 100c includes a distance detecting unit 130 for measuring the imaging distance.

FIG. 7 is a block diagram of the stereoscopic X-ray imaging apparatus 100c according to the third embodiment. Note that any part of the configuration common with the first embodiment is denoted with the same reference numeral and the description thereof is omitted. As in FIG. 7, a stereoscopic X-ray generating unit 12 includes the distance detecting unit 130 and an attitude detecting unit 131. The distance detecting unit 130 detects the actual imaging distance, and sends the detected result to a controller 10. Various publicly-known non-contact range finders, for example, are applicable as the distance detecting unit 130. The attitude detecting unit 131 detects an attitude of the stereoscopic X-ray generating unit 12, and sends the detected result to the controller 10. Various publicly-known gyro sensors are applicable as the attitude detecting unit 131. Based on the detected result of the attitude by the attitude detecting unit 131, the controller 10 corrects the imaging distance detected by the distance detecting unit 130.

Then, the controller 10 compares the imaging distance detected by the distance detecting unit 130 (may be a corrected imaging distance) and a currently-set "appropriate stereoscopic diaphragm distance $D_j$". Then, the controller 10 drives the diaphragm unit 122 in order to adjust the "appropriate stereoscopic diaphragm distance $D_j$" to be equal to the imaging distance detected by the distance detecting unit 130.

Fourth Embodiment

Next, a fourth embodiment of the present invention is described with reference to FIG. 3. The first to third embodiments are configured to change the stereoscopic diaphragm distance. On the other hand, the fourth embodiment is configured to adjust positions and the sizes of right and left X-ray radiation fields $G_R$ and $G_L$ by changing an angle of convergence θ of an X-ray radiated by right and left X-ray tubes 121R and 121L. The configuration of the stereoscopic X-ray imaging apparatus according to the fourth embodiment is different from the configuration according to the first embodiment in that the stereoscopic distance displaying unit 111 is replaced by a convergence angle displaying unit. The convergence angle displaying unit displays the appropriate angle of convergence. The appropriate angle of convergence means an angle of convergence in which the X-ray can be radiated so that the right and left X-ray radiation fields $G_R$ and $G_L$ overlap (correspond) with each other, and no unnecessary radiation exposure occurs. Note that any other configuration is common with the first embodiment.

As in FIG. 3, a controller 10 can change the angle of convergence θ by controlling the right and left inner blades 123R and 123L and the right and left outer blades 124R and 124L. In the controller 10, a relationship between the angle of convergence θ and positions of the right and left inner blades 123R and 123L and the right and left outer blades 124R and 124L is stored. An operator specifies the angle of convergence θ by operating an operating unit 11. By doing so, the controller 10 reads the positions of the inner blades 123R and 123L and the right and left outer blades 124R and 124L corresponding to the angle of convergence θ specified by the operator, and moves the inner blades 123R and 123L and the right and left outer blades 124R and 124L to the positions that have been read. In this way, the controller 10 adjusts the angle of convergence θ by driving the inner blades 123R and 123L and the right and left outer blades 124R and 124L. In such a configuration, the positions and the sizes of the right and left X-ray radiation fields $G_R$ and $G_L$ can be adjusted. Note that, as in FIG. 3, a distance between the right and left X-ray tubes 121R and 121L does not change. Therefore, the controller 10 changing the angle of convergence of the X-ray radiated by the right and left X-ray tubes 121R and 121L and the controller 10 changing the imaging distance have the same meaning.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disc (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-124101, filed May 31, 2012, which is hereby incorporated by reference herein in its entirety.

What is claimed is:

1. A stereoscopic X-ray imaging apparatus comprising:
   a plurality of X-ray sources;
   a diaphragm unit in which a plurality of openings is formed, X-rays radiated by the plurality of X-ray sources passing through the plurality of openings, respectively;
   an X-ray sensor on which the X-ray radiated by each of the plurality of X-ray sources is projected;
   an adjuster configured to adjust positions and sizes of the plurality of openings; and
   a plurality of visible light sources each configured to radiate a visible light to the X-ray sensor in the same area as that of a different one of the plurality of X-ray sources through each of the plurality of openings,
   wherein spectra of the visible light emitted by the plurality of visible light sources are different from each other.

2. The stereoscopic X-ray imaging apparatus according to claim 1,
   wherein the adjuster adjusts positions and sizes of the openings based on an imaging distance between the plurality of X-ray sources and the X-ray sensor.

3. The stereoscopic X-ray imaging apparatus according to claim 1, further comprising a visible light image capturing unit configured to image a visible light image formed of the visible light radiated by the plurality of visible light sources,
   wherein the adjuster adjusts the positions and the sizes of the openings based on the visible light image imaged by the visible light image capturing unit.

4. The stereoscopic X-ray imaging apparatus according to claim 1, further comprising a distance detecting unit configured to detect a distance between the plurality of X-ray sources and the X-ray sensor,
   wherein the adjuster adjusts the positions and the sizes of the openings based on the distance detected by the distance detecting unit.

5. The stereoscopic X-ray imaging apparatus according to claim 1, wherein the adjuster adjusts an angle of convergence of the X-ray radiated by the plurality of X-ray sources.

6. The stereoscopic X-ray imaging apparatus according to claim 1, further comprising a display control unit configured to cause a display unit to display information indicating a distance between the plurality of X-ray sources and the X-ray sensor.

7. The stereoscopic X-ray imaging apparatus according to claim 6, wherein the display control unit is configured to cause the display unit to, in a case that an anti-scatter grid is used in the X-ray imaging apparatus, display information indicating a distance for the anti-scatter grid.

8. The stereoscopic X-ray imaging apparatus according to claim 1, further comprising a display control unit configured to cause a display unit to, change display of a type of information, based on whether or not an anti-scatter grid is used in the X-ray imaging apparatus.

9. The stereoscopic X-ray imaging apparatus according to claim 1, further comprising an operation unit configured to receive an input from a user to adjust at least one of the positions and sizes of the plurality of openings.

10. The stereoscopic X-ray imaging apparatus according to claim 1, further comprising a display control unit configured to cause a display unit to display images obtained from the X-ray sensor on which the X-ray radiated by the plurality of X-ray sources is projected on the same area.

11. The stereoscopic X-ray imaging apparatus according to claim 1, wherein the adjuster adjusts the positions of the plurality of openings, so that the plurality of openings is positioned in line symmetry with respect to a line through a center position of X-ray foci of the plurality of X-ray sources.

12. A stereoscopic X-ray imaging apparatus comprising:
    a plurality of X-ray sources;
    a diaphragm unit in which a plurality of openings is formed, X-rays radiated by the plurality of X-ray sources passing through the plurality of openings, respectively;
    an X-ray sensor on which the X-ray radiated by each of the plurality of X-ray sources and a visible light radiated by each of a plurality of visible light sources are projected; and a controller configured to control positions and sizes of the plurality of openings based on an imaging distance between the plurality of X-ray sources and the X-ray sensor.

13. The stereoscopic X-ray imaging apparatus according to claim 12, further comprising the plurality of visible light sources configured to radiate the visible light to the X-ray sensor in the same area as each of the plurality of X-ray sources through each of the plurality of openings,
   wherein each of the plurality of visible light sources radiates the visible light having a spectrum different from each other.

14. The stereoscopic X-ray imaging apparatus of claim 12, further comprising:
   a visible light sensor having a two-dimensional detection area, configured to detect visible light emitted from the plurality of visible light sources, to obtain a visible light image.

15. The stereoscopic X-ray imaging apparatus of claim 14, wherein the controller is configured to, based on the obtained visible light image, determine a state of overlapping of areas on which the plurality of the visible light sources is projected.

16. The stereoscopic X-ray imaging apparatus of claim 14, wherein the controller is configured to, based on the obtained visible light image, adjust the positions and the sizes of the plurality of openings.

* * * * *